United States Patent
Sullivan et al.

(10) Patent No.: US 7,867,267 B2
(45) Date of Patent: *Jan. 11, 2011

(54) STENT DELIVERY SYSTEM WITH NESTED STABILIZER AND METHOD OF LOADING AND USING SAME

(75) Inventors: Jason R. Sullivan, Wayne, NJ (US); John Keller, Shelton, CT (US); Matthew S. Ketterer, Quakertown, PA (US); Kristian J. DiMatteo, Watertown, MA (US); Michael J. Bettuchi, Randolph, MA (US); Ellen Golds, Hastings-on-Hudson, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1257 days.

This patent is subject to a terminal disclaimer.

(21) Appl. No.: 10/616,267

(22) Filed: Jul. 9, 2003

(65) Prior Publication Data
US 2004/0106977 A1    Jun. 3, 2004

Related U.S. Application Data

(63) Continuation of application No. 09/574,418, filed on May 19, 2000, now Pat. No. 6,607,551.

(60) Provisional application No. 60/134,985, filed on May 20, 1999, provisional application No. 60/157,335, filed on Oct. 1, 1999.

(51) Int. Cl.
    *A61F 2/84*    (2006.01)
(52) U.S. Cl. ................................ 623/1.11; 606/108
(58) Field of Classification Search ............ 623/1.15, 623/1.11, 1.12, 1.23; 606/108; 604/103.03, 604/103.06, 103.07, 103.08
See application file for complete search history.

(56) References Cited

U.S. PATENT DOCUMENTS 4,950,227 A    8/1990    Savin et al.

(Continued)

FOREIGN PATENT DOCUMENTS

EP    0 775 470    5/1997

(Continued)

OTHER PUBLICATIONS

U.S. Appl. No. 09/573,273, Hijikema, entire document.
International Search Report for corresponding PCT Application PCT/US 00/14038, dated Sep. 13, 2000.

(Continued)

*Primary Examiner*—Anhtuan T Nguyen
*Assistant Examiner*—Ryan J Severson
(74) *Attorney, Agent, or Firm*—Brooks, Cameron & Huebsch, PLLC

(57) ABSTRACT

A stent delivery system deploys a stent having an inner periphery that defines an interior space extending lengthwise along at least a part of the stent and comprising at least one segment having relatively low column strength. The stent delivery system comprises a stabilizer which is disposed within the stent interior space and has a surface element adapted to engage the stent inner periphery in a region containing the low-column-strength segment. The surface element may comprise a sleeve or a coating having a high friction surface adapted to transmit adequate shear force to the stent to move the stent relative to the outer sheath upon deployment. Alternatively, or in addition, the surface element can include at least one radial protuberance. The protuberances may comprise rings of various cross-sections, axial lengths, or space sizes therebetween, or may be in the form of discrete barbs, bumps, or inflatable knobs arranged in a ringed configuration or helical pattern about the stabilizer. The stabilizer may also comprise an inner core and a heat-moldable compression sleeve surrounding the inner core, the heat-moldable compression sleeve having an outer surface comprising a plurality of protuberances defined by a thermal imprint of the stent inner periphery on the compression sleeve outer surface. A method for delivering a stent using a stent delivery system as described herein is also disclosed, as is a method for loading a stent and stabilizer having a heat-moldable compression sleeve into a stent delivery system.

22 Claims, 6 Drawing Sheets

U.S. PATENT DOCUMENTS

| | | | |
|---|---|---|---|
| 5,026,377 A | | 6/1991 | Burton et al. |
| 5,037,427 A | * | 8/1991 | Harada et al. ............... 606/108 |
| 5,201,757 A | | 4/1993 | Heyn et al. |
| 5,201,901 A | | 4/1993 | Harada et al. |
| 5,480,423 A | * | 1/1996 | Ravenscroft et al. ....... 623/1.11 |
| 5,484,444 A | * | 1/1996 | Braunschweiler et al. .. 623/1.11 |
| 5,562,726 A | | 10/1996 | Chuter |
| 5,569,295 A | | 10/1996 | Lam |
| 5,591,222 A | | 1/1997 | Susawa et al. |
| 5,609,627 A | | 3/1997 | Goicoechea et al. |
| 5,645,559 A | * | 7/1997 | Hachtman et al. ............ 623/1.2 |
| 5,683,451 A | | 11/1997 | Lenker et al. |
| 5,702,418 A | * | 12/1997 | Ravenscroft ............... 623/1.11 |
| 5,709,703 A | | 1/1998 | Lukic et al. |
| 5,749,921 A | | 5/1998 | Lenker et al. |
| 5,755,777 A | | 5/1998 | Chuter |
| 5,824,041 A | | 10/1998 | Lenker et al. |
| 5,843,167 A | | 12/1998 | Dwyer et al. |
| 5,902,334 A | | 5/1999 | Dwyer et al. |
| 5,913,871 A | | 6/1999 | Werneth et al. |
| 5,980,532 A | | 11/1999 | Wang |
| 6,033,388 A | | 3/2000 | Nordstrom et al. |
| 6,056,906 A | | 5/2000 | Werneth et al. |
| 6,077,295 A | * | 6/2000 | Limon et al. ............... 623/1.11 |
| 6,110,142 A | | 8/2000 | Pinchuk et al. |
| 6,245,099 B1 | * | 6/2001 | Edwin et al. ............... 623/1.13 |
| 6,302,893 B1 | * | 10/2001 | Limon et al. ................ 606/108 |
| 6,576,006 B2 | * | 6/2003 | Limon et al. ............... 623/1.11 |

FOREIGN PATENT DOCUMENTS

| | | |
|---|---|---|
| EP | 0 834 293 | 4/1998 |
| JP | 05-038367 | 2/1993 |
| WO | WO 95/33422 | 12/1995 |
| WO | WO 98/14233 | 4/1998 |
| WO | WO 98/53761 | 12/1998 |

PUBLICATIONS

Written Opinion dated Feb. 14, 2001 for International Application No. PCT/US00/14038.

* cited by examiner

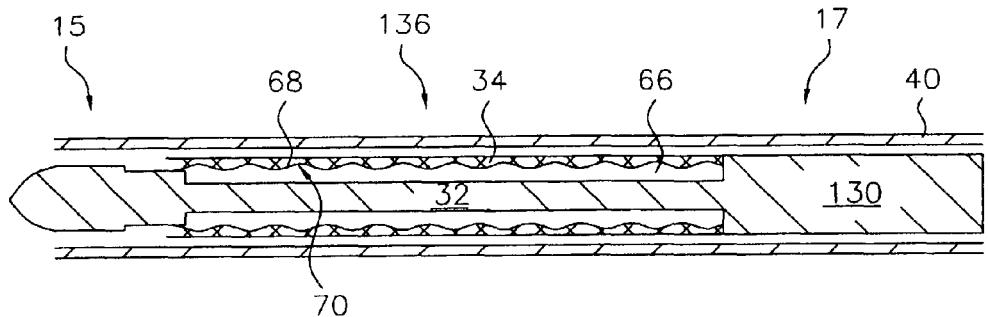
FIG. 7
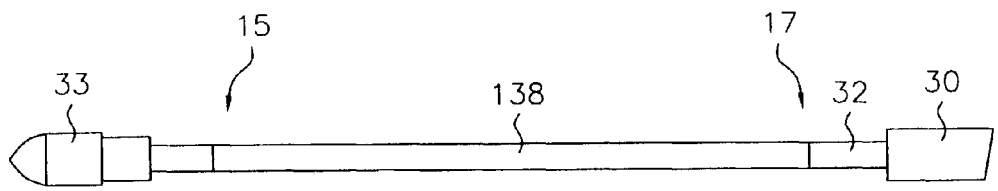
FIG. 8
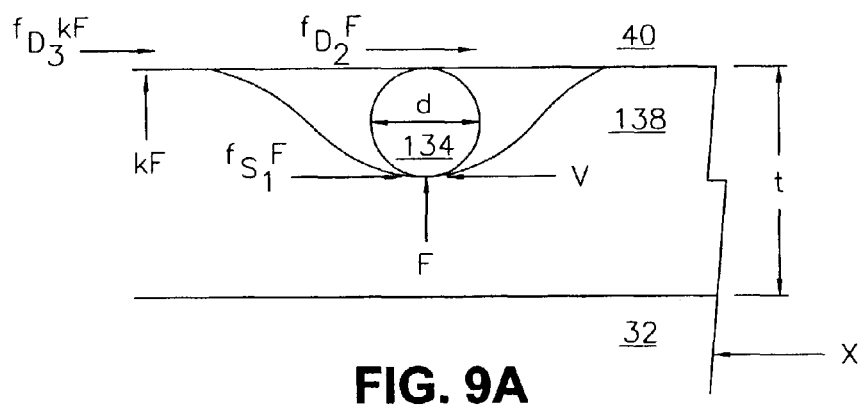
FIG. 9A
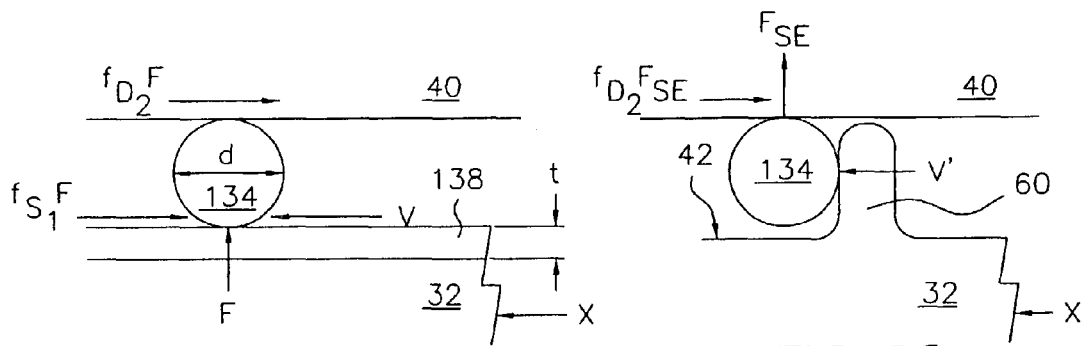
FIG. 9B     FIG. 9C

STENT DELIVERY SYSTEM WITH NESTED STABILIZER AND METHOD OF LOADING AND USING SAME

This application is a continuation of U.S. patent application Ser. No. 09/574,418, filed on May 19, 2000 now U.S. Pat. No. 6,607,551.

CROSS-REFERENCE TO RELATED APPLICATIONS

This application claims priority based upon U.S. Provisional Application Ser. No. 60/134,985, filed May 20, 1999, and U.S. Provisional Application Ser. No. 60/157,335, filed Oct. 1, 1999.

TECHNICAL FIELD

This invention relates generally to endoluminal grafts or "stents" and, more specifically, to stent delivery systems or "introducers".

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. As used herein, however, the term "stent" is a shorthand reference referring to a covered or uncovered such stent.

A covered stent may be used, for example, to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent deployment system or "introducer" to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a preconditioned expanded configuration.

Referring now to a typical prior art stent introducer as seen in FIG. 1A and FIG. 1B, there is shown a standard pre-loaded stent delivery system 10 comprising an outer sheath 12, a compressed stent 14 loaded therein, and a conventional stabilizer 16 loaded adjacent to the proximal end 17 of the stent. As used herein, the term "proximal" refers to the end closer to an access location outside the body whereas "distal" refers to the farther from the access location. The term "stabilizer" is used in the art to describe component 16 of stent delivery systems used to stabilize or prevent retraction of stent 14 when sheath 12 is retracted, thus effecting deployment of the stent into a desired location by forcing relative movement between the sheath and the stent.

Delivery system 10 also may comprise a catheter tip 20 at its distal end attached to an internal sheath 23 that runs through the delivery system through inner lumen 22 in stabilizer 16, as shown in FIG. 1A. A stabilizer handle 26 is typically located at the proximal end of stabilizer 16, outside the body lumen. Internal sheath 23 may guide the delivery system through the body lumen over a guidewire (not shown) to the area to be repaired, or may be adapted for inflating a balloon (if applicable), and/or for flushing the system. The delivery system may additionally have radiopaque markers (not shown) at selected locations therein to be used for fluoroscopic guidance of the system through the body lumen.

To deploy stent 14, delivery system 10 is threaded through the body lumen to a desired location for stent deployment. Outer sheath 12 is then retracted, and stabilizer 16 acts as a stabilizer to keep stent 14 from retracting with the sheath. As outer sheath 12 retracts, stent 14 is exposed and expands into place in the body lumen to be repaired.

Some stents have relatively low column strength either along their whole length or in discrete sections thereof. Their low column strength may be an inherent result of a flexible stent architecture. Such low-column-strength stents or stent sections are easily deformed in a longitudinal direction, and thus longitudinal force is not transmitted along the length of the stent. This inability to transmit longitudinal force may result in such stents collapsing in an accordion fashion as the sheath is retracted or as the stent is ejected by movement of the stabilizer, when the stent is deployed using a standard stabilizer positioned at the proximal end of the stent. This collapsing is caused primarily by frictional forces, such as frictional forces between the sheath and the stent (in the case where the stent is deployed by retraction of the sheath) or between the stent and the body lumen (in the case where the stent is deployed by ejection). Thus, a low column strength segment is one which tends to collapse due to frictional forces upon deployment of the stent by a conventional stabilizer positioned at the proximal end of the stent. This collapsing may cause damage to the stent or incorrect deployment. Thus, it is desirable to employ a stent-stabilizer combination that avoids such collapse.

U.S. Pat. No. 5,702,418 to Ravenscroft, of common assignment with the present invention, discloses an introducer comprising a stabilizer having an inner core that underlies a compressed stent within a sheath. The core has one or two proximal rings attached to and extending radially from the surface of the inner core for engaging the compressed stent at the proximal end thereof. Ravenscroft further describes but does not illustrate stabilizer embodiments having additional rings, rings including slots for receiving portions of the stent overlying the rings, and rings formed or defined by a plurality of protuberances or fingers extending from the core to engage and interlock the stent minimum inner diameter at the proximal end thereof. The purpose of these rings, according to Ravenscroft, is to allow selective retraction and deployment of the stent.

Thus, it is known to have rings or protuberances that engage the inner diameter of the stent, but only with respect to one or more rings that engage the proximal end of the stent to enable selective retraction and deployment of the stent. There remains a need, therefore, for a means to facilitate deployment of endoluminal stents with relatively low column strength.

SUMMARY OF THE INVENTION

In accordance with this invention, there is provided a stent delivery system for receiving, endoluminally transporting, and endoluminally deploying an elongated stent for holding open a body lumen, which system facilitates the use of stents with low column strength. The stent delivery system comprises a stent, an overlying sheath, and a stabilizer. The stent has an inner periphery that defines an interior space extending lengthwise along at least a part of the stent, at least one longitudinal segment of which may comprise relatively low column strength (or reduced column strength as compared to other parts of the stent), in that such segment is easily collapsed longitudinally. Such a low column strength segment may comprise all or nearly all the length of the stent. The stent is adapted to be radially compressed and loaded within the delivery system for introduction into the body lumen and expanded for deployment within the body lumen. The sheath overlies the compressed stent during introduction of the stent within the body lumen from a proximal access location to a distal deployment location. The stabilizer is disposed within the stent interior space and has at least one surface element adapted to engage the stent inner periphery in a region containing the low-column-strength segment.

The stent may comprise a plurality of peripheral members disposed in succession along the length of the stent (i.e. longitudinally), in which case the stabilizer comprises at least one surface element adapted to engage individual peripheral elements in a manner capable of imparting a longitudinal force thereto. The stabilizer may comprise a plurality of protuberances positioned peripherally about the stabilizer such that the stabilizer engages the peripheral elements in a plurality of peripheral locations. The engagement between the protuberance and the peripheral element may be a frictional, engagement, or a direct mechanical engagement, for example where the protuberance penetrates an area of open space between peripheral elements of the stent.

The stabilizer typically comprises a surface element comprising one or more frictional surface areas, protuberances, or protrusions axially spaced along the stabilizer underlying the stent from a distal end to a proximal end of the low-column-strength segment, which may comprise the entire stent. The stabilizer may further comprise an inner core wherein the surface element is a sleeve or coating about the inner core. The surface element may further comprise radial protuberances in the form of rings about the inner core. The rings may be of various' cross-sections, such as rectangular or triangular, may have varying lengths in one section of the stabilizer relative to another, and may have spaces of various sizes between adjacent rings. The rings may be locking rings that further comprise protrusions that penetrate into the open space between peripheral stent elements. Instead of rings, the protuberances may instead be discrete barbs, bumps, or inflatable knobs that may be arranged in a ringed configuration about the stabilizer, or may be axially and peripherally spaced in a helical pattern.

Alternatively, the stabilizer may comprise an inner core and a heat-moldable compression sleeve surrounding the inner core, the heat-moldable compression sleeve having an outer surface comprising a plurality of surface elements defined by a thermal imprint of the stent inner periphery on the compression sleeve outer surface. The invention also comprises a corresponding method for loading a stent into the stent delivery system described above. The method comprises inserting the heat-moldable portion of the stabilizer within the stent interior space, compressing the stent so that the outer surface of the heat-moldable portion is in contact with the stent inner periphery, inserting the stent and underlying stabilizer within the outer sheath, and heating the stent delivery system to thermally imprint the heat-moldable portion outer surface with an uneven topography conforming to the stent inner periphery.

The stabilizer may instead comprise about its inner core an injection-molded sleeve having a similar structure to that described. In such an embodiment, the method for loading the stent comprises-radially compressing and loading the stent inside the sheath with the stabilizer inner core axially disposed within the stent interior space, and creating a sleeve over said inner core by injecting a thermoplastic material around the inner core to fill the interior space. The resulting injection-molded sleeve has an outer surface with an uneven topography conforming to the stent inner periphery.

The invention also comprises a method of delivering a stent using a stent delivery system as described herein, the method comprising urging the stent delivery system through the patient's body to a desired deployment location and displacing the sheath longitudinally relative to the stabilizer so that the protuberances engage the stent to displace the stent relative to the sheath.

BRIEF DESCRIPTION OF THE DRAWINGS

FIG. 7 is a longitudinal section illustration showing an exemplary stabilizer of the present invention comprising a thermally-imprinted or injection-molded sleeve over an inner core.

FIG. 8 is a side view illustration showing an exemplary low-profile stabilizer of the present invention having a thin, high-friction surface element.

FIGS. 9A-C are schematic illustrations, of exemplary stent and stabilizer embodiments of the present invention showing forces acting on the stent.

DETAILED DESCRIPTION OF THE INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1A:
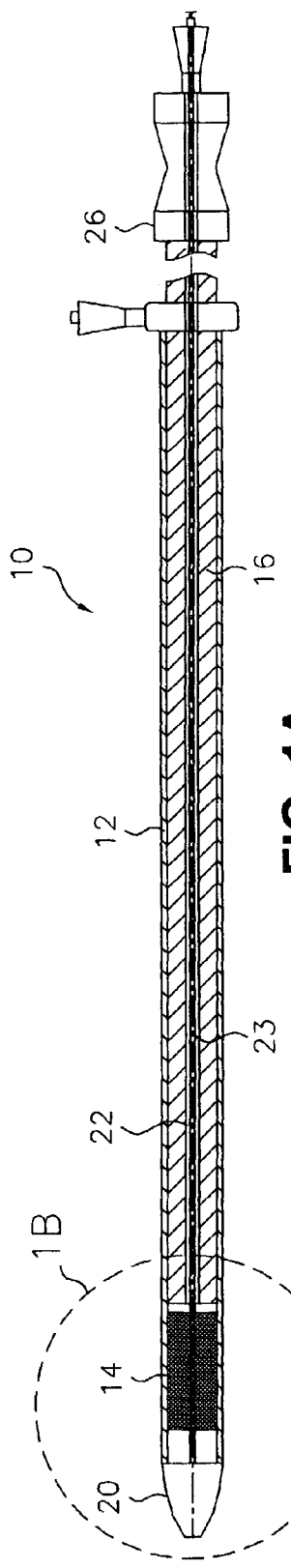
FIGS. 1A and 1B are longitudinal section illustrations of an exemplary stent delivery system of the prior art, and an enlarged portion thereof, respectively.
Figure 1B:
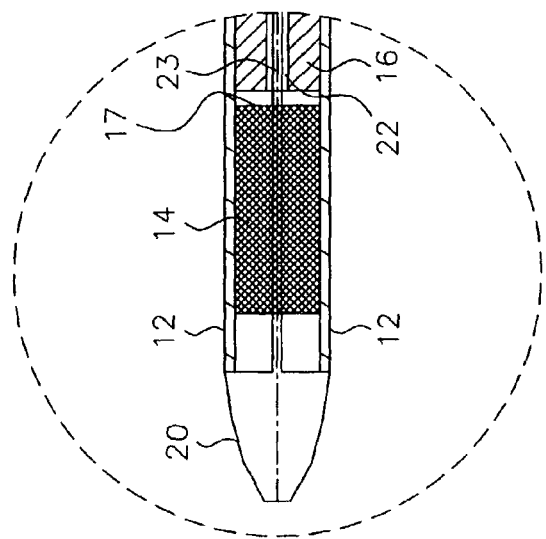
Figure 2A:
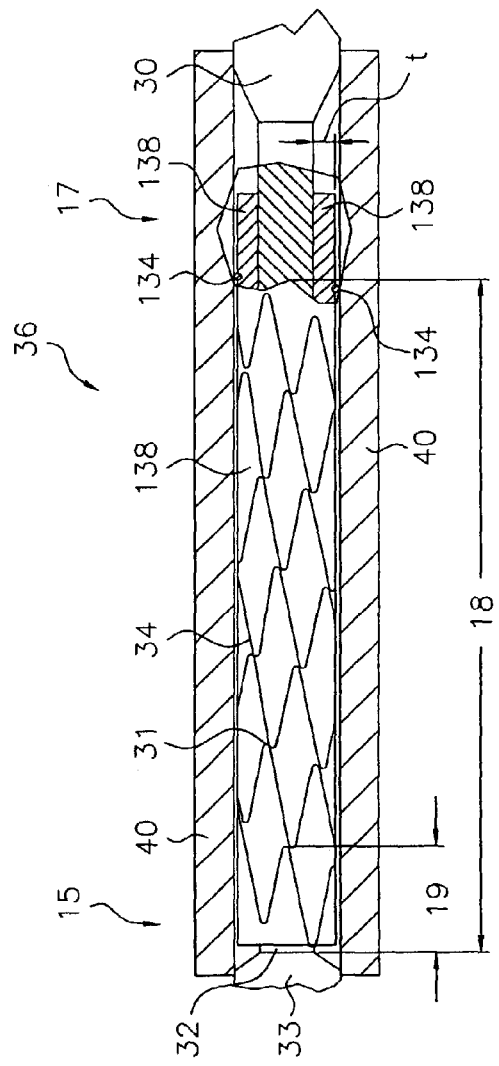
FIGS. 2A and 2B are side view partial cross-section illustrations of a portion of an exemplary stent delivery system according to the present invention.
Figure 2B:
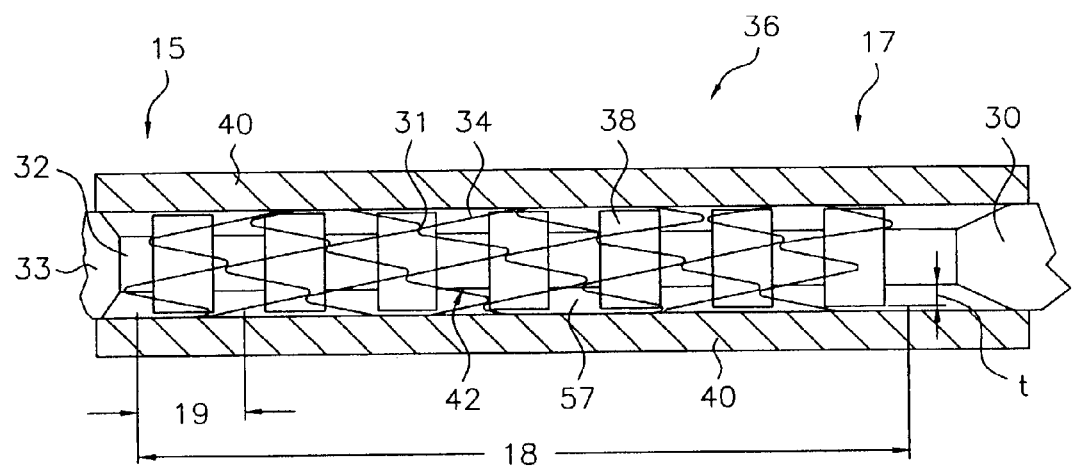

As shown in FIGS. 2A and 2B, exemplary stent delivery systems 36A and 36B, respectively, of the present invention each include a sheath 40 (shown in longitudinal-section) and a stabilizer 30A and 30B (shown in full) for deploying stent 34 relative to sheath 40. Stent 34 comprises a periphery, such as a wire structure, that defines an interior space therein through which stabilizer 30A or 30B is axially disposed. Stabilizer 30A or 30B comprises an inner core 32 having a surface 42 that underlies ("nests" within) the compressed stent during introduction into the body. Catheter tip 33 is attached to the distal end of stabilizer inner core 32, distal to an exemplary stent 34. As used herein, the term "stent delivery system" shall encompass both a completed assembly which is capable of deploying a stent or a subassembly which is capable of deploying a stent when combined with other components.

Although such device may also be referred to in the art as a "pusher", the term "stabilizer" is used herein throughout because the preferred method of deploying the stent as used herein does not actually comprise "pushing" the stent out of the sheath, but rather "stabilizing" the stent (holding it in place and preventing it from moving) while the sheath is retracted. Use of the term "stabilizer" herein refers to such a device adapted for any method of use known in the art, however, including as a pusher, and is not intended as a limitation thereof.

Exemplary stent 34, as shown, comprises wire members bent into a series of zig-zags having apex sections and struts therebetween, axially-opposing apex sections being circumferentially offset from one another except for one set of axially-opposing apexes per helical rotation that are connected together, such as by spot-welding, so that the series of successive connected apex sections form a helical spine. Other stents may not have a defined spine. Some of the stents shown and described in U.S. Pat. No. 5,404,377—Cragg, U.S. Pat. No. 5,609,627—Goicoechia et al., U.S. Pat. No. 5,575,816—Rudnick, and U.S. Pat. No. 4,655,771—Wallsten, which are incorporated herein by reference, may have low column strength depending on how they are made, among other factors. More specifically, in each case, the inherent stiffness and dimensions of the material of which the stent is constructed and the number and the nature of connections between stent elements will determine the column strength of the stent. For purposes of illustrating the present invention, stent 34 is assumed to be of low column strength throughout its length. In other embodiments, the stent used with the present invention may be of low column strength through only a part of its length with the nesting stabilizer of the present invention configured accordingly.

In exemplary stent 34, each peripheral element 19 as shown in FIGS. 2A and 2B comprises a 360-degree helical rotation of nitinol wire in a zig-zag pattern with adjacent hoops attached to one another by spot welds 31 between facing apices. Stent delivery systems 36A and 36B further comprise stabilizers 30A and 30B, respectively, adapted to engage the inner periphery of stent 34. "Engaging" in this sense is defined as imparting a longitudinal force thereto. This force may be a holding or stabilizing force that merely maintains the position of the stent and prevents the accordion-like collapse of the stent, or individual longitudinal sections thereof, as the sheath is retracted, or it may comprise actual movement of the stent out of the sheath with the sheath maintaining a constant position in the case of a non-self-expanding stent (e.g., a balloon-expandable stent).

Stabilizer 30A or 30B is adapted to engage the stent inner periphery or low-column-strength portion thereof in a manner than enables transfer of longitudinal force to the stent without collapsing the low-column-strength portion. Preferably, stabilizer 30A or 30B comprises a surface element underlying stent 34 from proximal end 17 to distal end 15 of the stent along low-column-strength segment 18 and adapted for such engagement of the stent inner periphery. For example, the surface element may comprise a high friction surface, such as covering 138 as shown in FIG. 2A, or a plurality of protuberances 38, such as the rings shown in FIG. 2B. Protuberances 38 may also be in frictional engagement with the inner periphery of stent 34, as shown in FIG. 2B, and/or may be in the form of protrusions that penetrate into the open space 57 between elements 19 of stent 34, such as for example protrusions 60A, 60B, or 60C of the stabilizer shown in FIG. 5.

Stabilizer 30A as shown in FIG. 2A may comprise a single surface covering 138 that makes frictional contact with the inner periphery of stent 34 over the entire length of the stent, such as for example, a silastic sleeve affixed overtop of core 32. Surface covering 138 may have a thickness t that is thicker than diameter d of stent wire 134, as is shown in FIG. 9A, or thinner than the diameter of stent wire 134, as shown in FIG. 9B. The smaller the thickness t, the smaller overall profile the delivery system may have. Low profile systems are desirable. Surface covering 138 may comprise a low durometer (soft) or heat-modable material that deforms to accept stent wire 34 in an indentation of the covering as shown in FIG. 9A. Covering 138 may instead comprise a high-friction surface that maintains a frictional engagement with stent 34 without significant indentation, as shown in FIG. 9B.

Generally, the frictional forces on stent 34 imparted by a thick, relatively low-hardness covering 138 may be depicted as shown in FIG. 9A. Radial force F is exerted on stent 34 as a reaction force proportional to the spring constant of surface covering 138 and the amount of deflection or indentation in that surface. Radial force F is also transmitted from the stent 34 to sheath 40. Some fraction kF of radial force F, where k<1, may also be transmitted directly from covering 138 to sheath 40 where the covering and sheath surfaces contact. It should be understood that, although shown in FIGS. 9A-C with respect to a single portion of a wire of stent 34, the total forces acting on stent 34 and sheath 40 equal the sums of all such forces along the length of stent 34 and covering 138 where there is similar contact surface area. The forces are depicted herein to illustrate concepts incorporated in the various embodiments and are not intended to show a full static or dynamic analysis of forces that may be acting upon each element. Similarly, the actual forces and precise calculations for deriving such forces may be more complex than the simple forces depicted and discussed herein.

Shear force V transmitted to stent 34 in the longitudinal direction is the relative force transmitted by stabilizer 30A to stent 34. This force may be derived either by pushing stabilizer 30A in the direction of force V or by holding the stabilizer steady while sheath 40 is retracted opposite the direction of force V. Shear force V must be less than the opposition force comprising the product of radial force F and the coefficient of static friction $f_{S1}$ between covering 138 and stent 34. Otherwise, stent 34 will slip relative to covering 138. Shear force V is greater than the opposition force comprising the product of force F and the coefficient of static friction $f_{S2}$ between sheath 40 and stent 34, causing sheath 40 to slip relative to stent 34. The relative motion of stent 34 is then opposed by the product of force F and the coefficient of dynamic friction $f_{D2}$ between sheath 40 and stent 34. Thus, the coefficient of static friction $f_{s1}$ between covering 138 and stent 34 is greater than the coefficients of friction $f_{S2}$ and $f_{D2}$ between stent 34 and sheath 40. For stabilizer 30A to move, the overall force X exerted on stabilizer 30A must also overcome the static opposition force $f_{S3}kF$ created by contact between covering 138 and sheath 40 and must counteract the dynamic opposition force $f_{D3}kF$ once the stabilizer is moving.

Because shear force V transmitted to stent 34 is limited by $f_{S1}F$ to prevent slip, increasing coefficient of friction $f_{S1}$, or increasing force F serves to increase the maximum force V able to be transmitted. Force F can be increased by increasing the spring constant or the amount of resiliency of the covering material, or by increasing the outside diameter of covering 138 while keeping the inside diameter of sheath 40 constant, thus increasing the amount of deflection or indentation of covering 138 when stabilizer 30A is placed within sheath 40 inside stent 34. Increasing force F in this manner also increases the force transmitted from the stent 34 to sheath 40 and from covering 138 to sheath 40, however, thus increasing the opposing frictional forces to shear force V, and thereby requiring a larger overall force X to be exerted on stabilizer 30A for deployment. The overall force X exerted on stabilizer 30A required to initiate and sustain relative motion of stent 34 with respect to sheath 40 may be minimized by decreasing the coefficients of friction $f_{S2}$, $f_{D2}$, $f_{S3}$, and/or $f_{D3}$ and/or by reducing the surface area of contact between covering 138 and sheath 40, and/or by decreasing radial force F. It is desirable to maximize shear force V transmitted to stent 34 for a minimum overall force X exerted on stabilizer 30A.

One way of reducing the overall force X is to reduce the frictional opposition force between sheath 40 and covering 138 and the amount of radial force transmitted to sheath 40 from stent 34 by reducing the amount of surface area where covering 138 contacts sheath 40 and/or stent 34. Thus, in the embodiment shown in FIG. 2B, discrete protuberances 38 underlie the low-column-strength segment 18 of stent 34 in the form of rings of covering 138. These protuberances 38, as shown in FIG. 2B, may comprise ring sections of a silastic sleeve that are affixed to core 32. Such protuberances 38 still have some area of direct contact with sheath 40 as well as still transmit some radial force F indirectly to sheath 40 through stent 34.

Another way of reducing the overall force X is to eliminate all direct contact between covering 138 and sheath 40, such as is shown in the stabilizer embodiment depicted in FIG. 8 that results in forces generally as shown in FIG. 9B. Such an embodiment may have a thickness t that is less than the diameter of the wire in stent 34, and in fact may be a coating as thin as 0.002 to 0.02 inches. Such a thin coating may typically be designed to impart a lesser radial force F to stent 34 (and accordingly to sheath 40) than the embodiment shown in FIG. 9A, but may therefore have a greater coefficient of friction $f_{S1}$, so that shear force V imparted to stent 34 is still sufficient to overcome the frictional opposition force between sheath 30A and stent 34. Thus, covering 138 may have a high coefficient of friction, such as is supplied by a tacky or sticky surface. For example, suitable materials of construction may include silicone, urethane, pressure-sensitive adhesives or low-durometer or heat-moldable plastics. Such a covering 138 may be provided merely by taking inner core 32, which may be, for example, a braided polyimide extrusion, and dipping it in or spraying on it, for example, a pourable silicone elastomer. The coated stabilizer may then be adjusted to a desired outside diameter, such as by pulling the stabilizer through a hole having a known inner diameter, to provide covering 138 with the desired thickness. The coating is then cured. Suitable silicone elastomers may include cross-linked silicone gels typically available with as low as a 3 Shore A durometer to as high as a 40 Shore A durometer. Such cross-linked silicones can also be proportionally mixed to achieve any desired durometer reading within the low to high range. The recited ranges are intended only as an example, and should not be construed as a limitation on the invention.

In another embodiment, the amount of friction imparted to sheath 40 may be minimized and the amount of force transmitted to stent 34 maximized by providing protuberances in the form of protrusions 60, such as are shown, for example, in FIG. 6. Such protrusions impart forces as illustrated in FIG. 9C. In this case, force V' acting on stent 34 is a direct force imparted by protrusion 60 onto stent 34, and is not limited by friction between stabilizer 30A and stent 34. In one variation of this embodiment, shown in FIG. 9C, protrusions 60 do not touch sheath 40 at all, and stabilizer 30A may contact stent 34 only at protrusion 60 and not on the axial surface 42 of core 32 of stabilizer 30A. In such an embodiment, the only opposition to force X may be the product of spring-elastic force $F_{SO}$ imparted by stent 34, where applicable (where stent 34 is a self-expanding stent having such an inherent force), multiplied by the coefficients of friction $f_{S2}$ (at rest) or $f_{D2}$ (in motion). In other embodiments, protrusions 60 may touch sheath 40, but the small contact area of the protrusions minimizes the frictional resistance between the protrusions and the sheath.

The embodiments having forces as illustrated in FIGS. 9B and 9C have an additional advantage of having a low profile. That is, embodiments having these designs do not require a substantial thickness between inner core 42 and sheath 40 that adds to the diameter of the overall introducer. In such embodiments, the distance between inner core 42 and sheath 40 may be as small as the diameter of the wire comprising stent 34. Although some embodiments may have certain advantages over others, all the embodiments discussed above, and variations or combinations thereof, are encompassed broadly by the present invention in that they are adapted to engage the stent inner periphery in a region containing low-column-strength segment of the stent in a manner that enables transmission of longitudinal force to the stent.

Various exemplary stabilizer embodiments are shown in FIGS. 3A-8. These embodiments are adapted for use with stent delivery systems similar to system 36 as shown in FIGS. 2A and 2B. For clarity of the drawings, FIGS. 3A-6B, and 8 do not show the stent overlying each illustrated stabilizer; however, certain overlying stent regions, such as distal end 15, proximal end 17, and middle region 50, are still indicated relative to the corresponding underlying section of the stabilizer. Protuberances 38 may be in any of several configurations, including but not limited to rings, bumps, barbs, inflatable knobs, protrusions, and locking rings, and comprise various lengths and spacing patterns, specific examples of which are described herein below for illustration rather than limitation. In such exemplary configurations, the stabilizer may engage one or more peripheral elements of the stent in a single location on each element periphery or in multiple locations about the periphery such as with a number of discrete protuberances that form a broken ring or a helical pattern about the stabilizer or with unbroken or partial rings circumscribing the stabilizer. Thus, the engagement between the stabilizer and the stent that promotes transfer of longitudinal force from the stabilizer to the stent may be a frictional engagement, such as the engagement made by a sleeve or series of rings that fully underlie the stent, or may be a mechanical engagement where the protuberances penetrate open spaces between the stent wire structure.

Figure 3A:
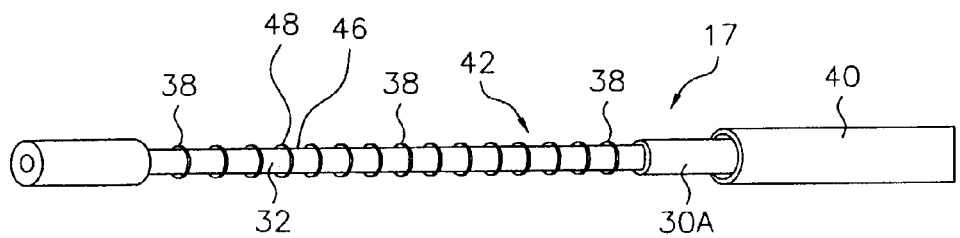
FIGS. 3A-3J are perspective or side view illustrations of various embodiments of stabilizers according to the present invention.
Figure 3B:
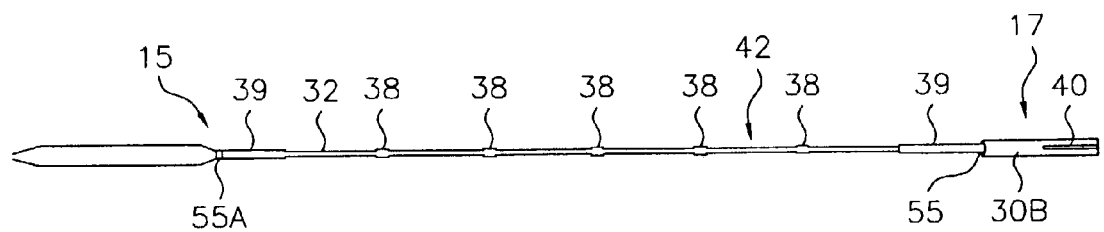
Figure 3C:
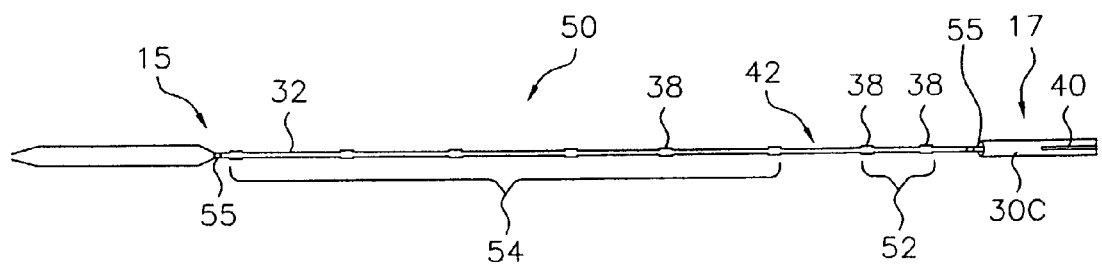
Figure 3D:
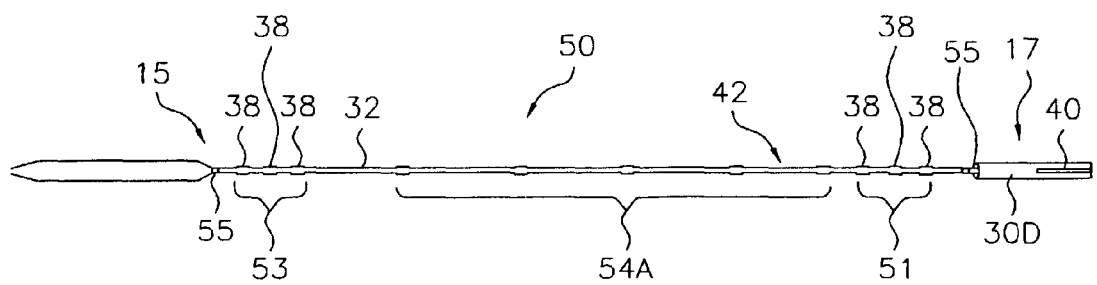
Figure 3E:
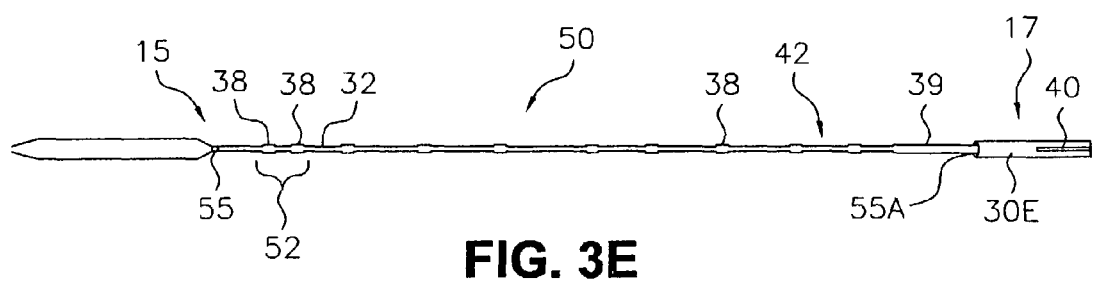
Figure 3F:
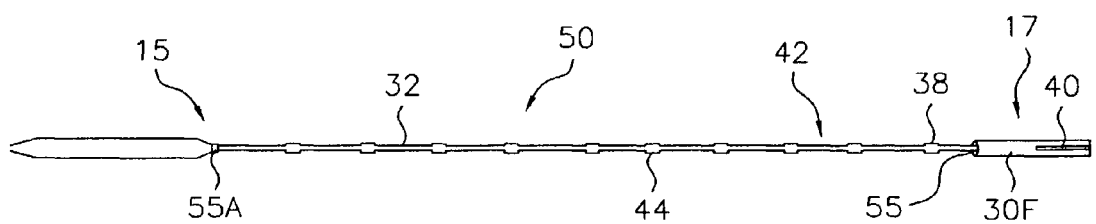
Figure 3G:
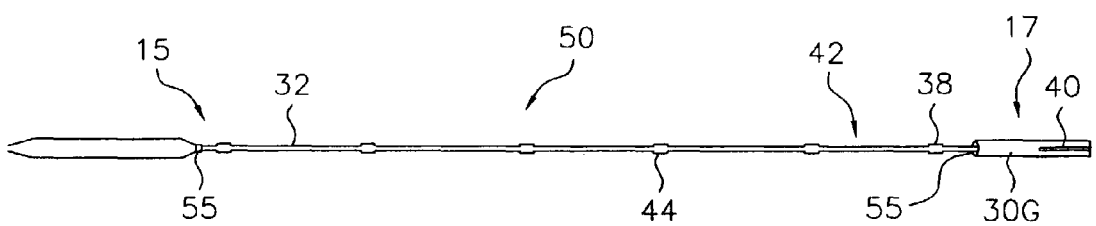

Thus, a stent delivery system in accordance with the present invention may comprise any of exemplary stabilizers $30_A$-$30_J$ as illustrated in FIGS. 3A through 3J, respectively. These stabilizers differ only in the configuration and location of protuberances 38 or 60. The protuberances may be in the form of rings 38 of approximately equal length and spaced evenly along the region of the stabilizer underneath the stent, as shown in FIGS. 3A, 3F, and 3G. Rings 38 may further comprise discrete annular sections 44 bonded to inner core 32 as shown in FIGS. 3F and 3G, or may comprise peaks 46 between which valleys 48 have been ground away from inner core 32 by a centerless grind technique or other process known in the art, as shown in FIG. 3A.

Figure 4A:
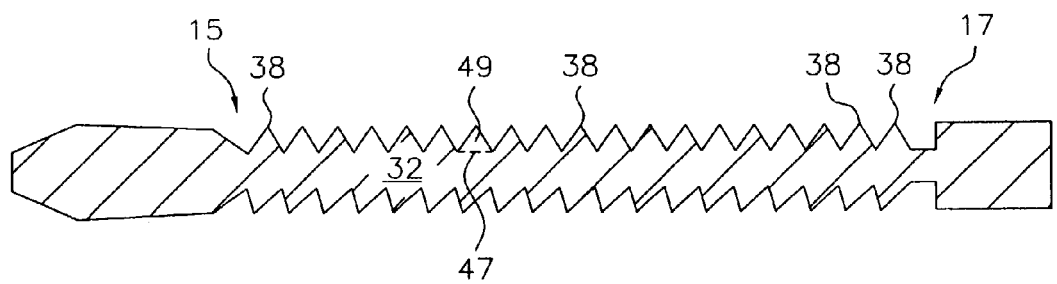
FIGS. 4A-4D are side view illustrations of longitudinal sections of exemplary stabilizers of the present invention, showing exemplary ring cross-sectional geometries.
Figure 4B:
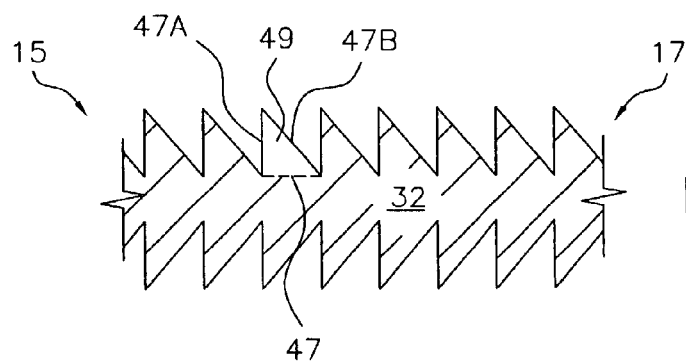
Figure 4C:
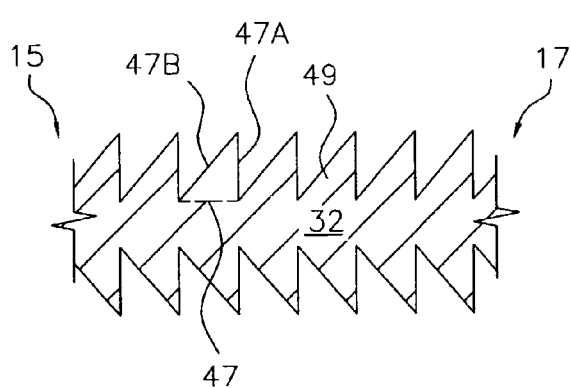
Figure 4D:
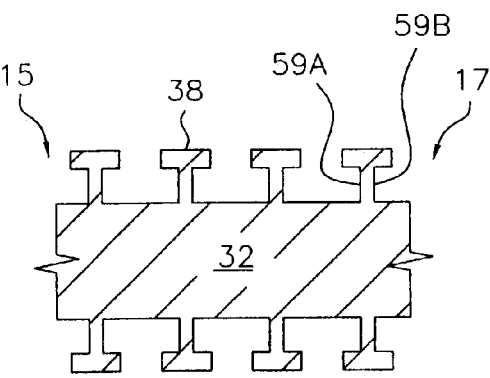

The rings according to the present invention may have a rectangular cross-sectional geometry as shown in. FIGS. 3B-3G, or referring now to FIGS. 4A-4C, rings 38 may have a triangular cross-sectional geometry. The triangular cross-sectional profile may, for instance, be in the form of an isosceles triangle 49 having a base 47 parallel to inner core 32 as shown in FIG. 4A, or the triangle may be a right (or near-right) triangle 49' having one side 47 parallel to the inner core, a second side 47A orthogonal to the inner core, and hypotenuse 47B diagonal to the inner core as shown in FIGS. 4B and 4C. Hypotenuse 47B may be angled distally from the inner core as shown in FIG. 4B, or proximally from the inner core as shown in FIG. 4C, depending on the properties desired for the interface between the stabilizer and the stent. The orientation shown in FIG. 4B may be particularly beneficial, however, as second side 47A provides better transfer of force to the stent in a distal direction than does the hypotenuse 47B in FIG. 4C. Other triangular configurations not specifically illustrated herein may also be used. Also, as shown in FIG. 4D, rings 38 may have a rectangular cross-section with a distal undercut 59A, a proximal undercut 59B, or both. Undercuts 59A and 59B provide a lip that engages the stent wire during deployment.

As shown in FIGS. 3B-3G, the stent (not shown) overlying inner core 32 comprises a middle region 50 intermediate distal end 15 and proximal end 17 of the stent. Rings 38 may be of approximately equal length, as shown in FIGS. 3C, 3D, 3F, and 3G. Furthermore, rings 38 may be spaced in a first pattern underlying stent middle region 50, and spaced in a second pattern at one or both of the stent distal 15 and proximal 17 ends, as shown in FIGS. 3C and 3D. As shown in FIG. 3C, there may be a set 52 of two rings 38 at proximal end 17 spaced closer together than the remaining set 54 of rings distributed underneath the stent middle region 50 and distal end 15. Alternately, as shown in FIG. 3D, there may be a set 51 of three rings 38 underlying stent proximal end 17 and a set 53 of three rings underlying stent distal end 15, each set 51 and 53 comprising rings spaced closer together than the remaining set 54A of rings underlying middle region 50.

The various rings may also have different lengths as well as different spacing patterns, as shown in FIGS. 3B and 3E. As shown in FIG. 3E, stabilizer $30_E$ comprises an end ring 39 underlying proximal end 17 of the stent, the end ring having a greater length than the length of the other rings, 38. As shown in FIG. 3B, a longer end ring 39 may also be positioned on inner core 32 underlying the stent distal end 15. Alternatively, as shown in FIG. 3E, an end ring 39 may be positioned underlying stent proximal end 17 and a set 52 of two rings 38 may be positioned underlying stent distal end 15, set 52 comprising rings spaced closer together than the rings in middle region 50.

In addition to or instead of different spacing patterns, the rings in one section may comprise a different material or slightly different diameter than the rings in another section. For instance, referring to FIG. 3D, sets 51 and 53 of rings 38 at ends 15 and 17 may comprise a different material than the rings in set 54A. The different material may be, for instance, a different plastic resin entirely, or may be merely another grade of the same resin having a different hardness. For example, silicone rings may have a hardness in a typical range of 45 to 59 Shore A durometer, whereas urethane rings may range from 55-85 Shore A durometer. Such tailoring of ring properties may be advantageous for balancing the hardness of the ring needed to transmit longitudinal force with the softness of the ring desired to prevent damage to the stent. Because different ring materials may transmit different magnitudes of radial force when compressed, different material properties may be used for different ring locations. For example, it may be desirable to use rings having a relatively greater hardness (and thus capable of transmitting relatively greater radial force than a relatively lesser hardness ring for an equivalent amount of compression) near the ends of the stent to provide anchoring of the stent. Thus, one embodiment may include urethane rings having a hardness of around 75 (Shore A durometer) in ring sets 51 and 53 and silicone rings having a hardness of around 50 (Shore A durometer) in ring set 54A. The recited hardness values are intended to provide only one example, however, and are not intended as a limitation of the invention. Similarly, sets 51 and 53 of rings 38 may be the same hardness material as the rings in set 54A but may have a slightly larger diameter. Because a slightly larger diameter ring experiences slightly more compression, the larger diameter ring exerts a greater reaction force, and thus may provide equivalent anchoring capabilities.

The various combinations of ring spacing, lengths, and geometry are not limited to the examples presented herein, but rather may be tailored to the needs of the specific stent and deployment circumstances. Also, as shown in FIGS. 3B-3G, the stabilizer may further comprise one or more radiopaque markers such as rings 55 and/or 55' positioned to provide "vision" via fluoroscopy to the attending surgical team. Radiopaque rings 55 and/or 55A may be positioned distally and/or proximally along the inner core 32, and may even be positioned under rings 38 and/or 39, such as rings 55A as shown in FIGS. 3B and 3E. In combination with selectively placed radiopaque markers disposed on the stent (not shown), such markers on the stabilizer may be used to visualize movement of the stent (or parts thereof) relative to the stabilizer. "Radiopaque marker" as used herein encompasses any discrete area of different radiopacity as compared to a surrounding area.

Figure 3H:
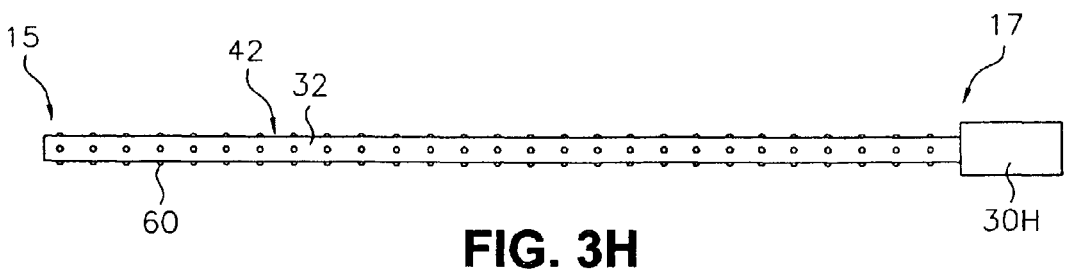
Figure 3I:
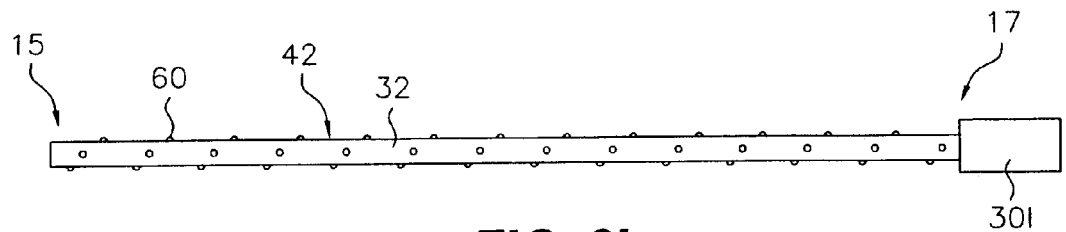
Figure 3J:
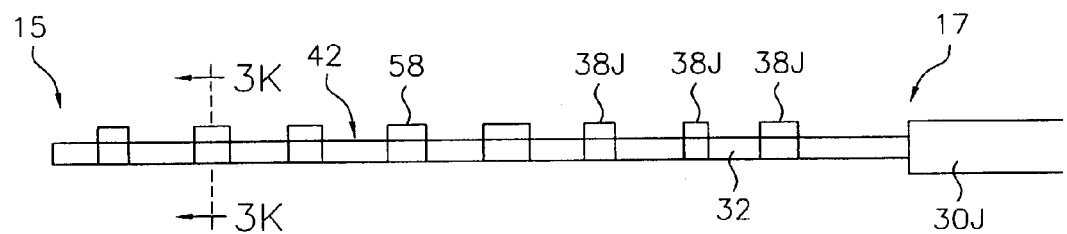
Figure 3K:
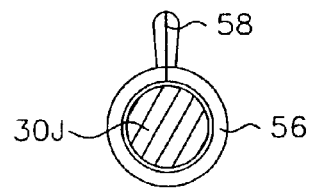
FIG. 3K is a cross-sectional illustration of the stabilizer of FIG. 3I along line 3K-3K, showing a cross section of a locking ring.

As shown in FIGS. 3J and 3K, rings $38_J$ on stabilizer $30_J$ may be locking rings 56. Locking rings 56 have the shape of a tubular ring crimped adjacent surface 42 of inner core 32 to produce protrusions 58. Locking rings 56 may be formed from such crimped tubes, or from molded or extruded rings known in the art, such as splined sleeves, having protrusions 58 and geometry similar to such tubular crimped locking rings. The term "locking rings" in the art often denotes metallic crimped tubes whereas the term "compression rings" tends to refer to molded or extruded plastic or polymer rings. As used herein, "locking rings" refers to the general ring geometry without any implied materials of construction, although non-metallic rings are preferred as being less damaging to the stent in use. The use of any locking rings may be especially suited for so-called "low-profile" delivery systems. Low-profile delivery systems are designed to minimize the overall diameter of the introducer. For stabilizers $30_{A-G}$ as shown in FIGS. 3A-3G, rings 38 and/or 39 that frictionally engage the inner periphery of the stent (not shown) add a certain diameter between the inner core 32 and the stent. As seen in FIG. 2, however, stent 34 may typically comprise a series of longitudinally-displaced peripheral elements 19 having one or more areas of open space 57 therebetween. Locking rings 56 do not add substantial diameter to the core; instead, protrusions 58 penetrate into the open space 57 between elements 19 so that the stent can still rest adjacent inner core 32 without any substantial separation distance added by the rings. Upon deployment, each protrusion 58 directly transfers longitudinal force via contact with element 19, rather than relying on indirect frictional force transfer. Each locking ring 56 may have multiple protrusions 58 extending from its circumference (not shown), and/or a series of locking rings may be aligned in a helical or other pattern (not shown) along inner core 32 so that the locking ring protrusions are pointed in more than one orientation.

Figure 5:
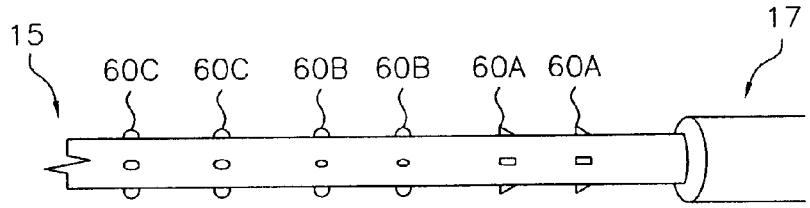
FIG. 5 is a side view illustration showing exemplary protuberance geometries according to the present invention.

Instead of using locking rings 56, a low-profile introducer may instead comprise protuberances in the form of protrusions 60 peripherally spaced in a ring about core 32 to engage the stent in multiple peripheral locations, as illustrated by stabilizers $30_H$ and $30_I$ in FIGS. 3H and 3I, respectively. Here, protrusions 60 can project through the open spaces 57 between peripheral elements 19 so that stent 34 (stent, spaces, and peripheral elements shown in FIG. 2) can rest against the inner core surface 42. Referring now to FIG. 5, such protrusions 60 may be further defined as a set of barbs $60_A$, bumps $60_B$, or inflatable knobs $60_C$. FIG. 5 shows each of the above exemplary protrusion types on one structure merely for illustrative purposes, although certain stabilizer embodiments may, but are not required to, include more than one type of protrusion. Barbs 60A may be oriented as shown in FIG. 5 for maximized transmission of distal force from the barb to the stent (not shown). Bumps $60_B$ and inflatable knobs $60_C$ may be in the same shape after formation, but the inflatable knobs can have controllable size, depending on the degree of inflation.

A stabilizer having inflatable knobs $60_C$ may be inflated by, for example, injecting saline solution into the stabilizer or by any inflation means known in the art. Inflatable knobs $60_C$ offer the capability of conforming to the shape of the stent when the stabilizer is inflated. Another capability of a stabilizer with inflatable knobs $60_C$ is that one stabilizer may be used for loading a stent into the stent delivery system and a different stabilizer used for deploying the stent. In suchecase, the inflatable stabilizer is merely deflated after loading the stent and then removed. Another inflatable stabilizer can then be inserted in its deflated configuration into the inner periphery of the stent and inflated when deployment is required. Thus, for example, if one stabilizer configuration is preferred for loading the stent and another configuration preferred for deploying the stent, specialized stabilizers may be developed for each specific purpose.

Figure 6A:
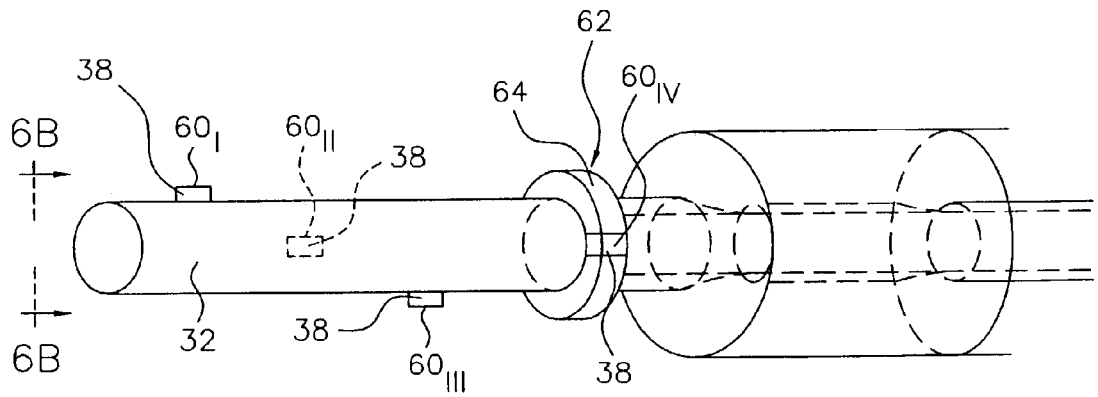
FIGS. 6A and 6B are illustrations of a perspective view and an end view, respectively, of an exemplary stabilizer of the present invention having a spiral distribution of protuberances.
Figure 6B:
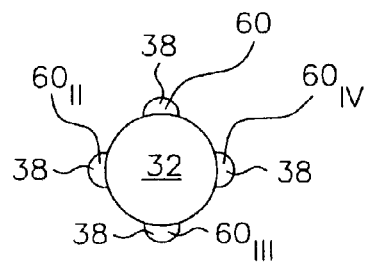

Rather than the protrusions forming or defining rings, the protrusions may extend radially from the inner core surface in a helical pattern, as shown in FIGS. 6A and 613. Protrusions $60_{I-IV}$ may be constructed of a ring 62 from which the majority 64 of the ring radius (shaded portion) is removed, leaving only protrusion $60_{IV}$, as shown in FIG. 6A. Protrusions $60_{I-IV}$ may be thus oriented in a helical pattern along the length of inner core 32.

Another structure enabling deployment of a low-column-strength stent is shown in FIG. 7. Stabilizer 130 comprises an inner core 32 and a sleeve 66 surrounding the inner core, where the sleeve outer surface 68 is imprinted with the topography of inner periphery 70 of stent 34. Such an imprinted surface 68 inherently includes a number of protuberances, and may be capable of engaging the stent and imparting longitudinal force to the stent both frictionally and mechanically. Sleeve 66 may comprise a heat-moldable compression sleeve or an injection-molded sleeve.

For the heat-imprinted compression sleeve, stent 34 is loaded into stent delivery system 136 by a method comprising the following steps. First, compressed stent 34 is placed overtop heat-moldable compression sleeve 66. Next, stent 34, compression sleeve 66, and inner core 32 are inserted inside an outer sheath 40. Then, stent delivery system 136 is heated, such as with a hot air gun, beyond the glass transition temperature of compression sleeve 66. This heating step thermally imprints the compression sleeve 66 outer surface 68 with an uneven topography conforming to the stent inner periphery 70. Inner core 32 and outer sheath 40 each preferably comprise a material, such as poly-ether-ether-ketone (PEEK) or polyimide (PI), having a heat deformation temperature greater than the heat deformation temperature of heat-moldable compression sleeve 66, so that only the compression sleeve deforms during the heating step. Compression sleeve 66 may be constructed of any common thermoplastic material, for example but not limited to, EVA, Pebax® resin, thermoplastically deformable nylons, and thermoplastic polyurethanes, such as Tecothane®.

Instead of compression sleeve 66 being a discrete sleeve that is subsequently heat-molded, sleeve 66 may instead be formed by injection molding. For example, stent 34 may be loaded inside sheath 40 with inner core 32 axially disposed therein, and one of the above-listed materials injected to fill the space between the inner core and the stent. In this way also, an imprinted sleeve 66 will be formed about core 32 having an outer surface 68 with an uneven topography conforming to the stent inner periphery 70.

Thus, according to the present invention, a stent is delivered and deployed by the following method steps. A stent delivery system, such as system 36A or 36B as shown in, FIGS. 2A or 2B, respectively, is inserted within the body of a patient. The delivery system may comprise a system having any of the stabilizer configurations described herein, but is illustrated with respect to FIGS. 2A and 2B for convenience. Delivery systems 36A and 36B include an outer sheath 40 overlying a compressed stent 34 at a distal end of the sheath, and an inner core 32 underlying the stent. High-friction covering 138 shown in FIG. 2A or one or more protuberances 38 shown in FIG. 2B on inner core surface 42 engage low-column-strength segment 18 of stent 34. The term "protuberance" encompasses, but is not limited to, the uneven topography of outer surface 68 of thermally imprinted compression sleeve 66 as shown in FIG. 7, the rings as shown in FIGS. 3A-G and 3J-K, or the bumps, barbs, knobs, or protrusions 60 as shown in FIGS. 3H, 3I, 5, 6A, and 6B. The engagement may be frictional, as imparted by the stabilizers shown in FIGS. 2A and 2B, mechanical, as imparted by the stabilizer shown in FIG. 9C, or both, as is imparted by molded stabilizer shown in FIG. 7. The method further comprises urging sheath 40 through the patient's body to a desired deployment location (not shown). Finally, sheath 40 is displaced longitudinally relative to inner core 32 such that the stabilizer engages the stent, transmits longitudinal force to the low-column-strength segment, and displaces the stent relative to the sheath without collapsing the low-column-strength segment. The longitudinal force may be transmitted frictionally, mechanically, or both. The relative motion between sheath 40 and inner core 32 may be accomplished by retracting the sheath or by advancing stabilizer 30.

With any of the stabilizer embodiments described above, in addition to facilitating deployment of stents having low-column-strength segments, the nested stabilizer of the present invention may additionally facilitate recapture during deployment of a stent. "Recapture" refers to retracting a partially deployed stent so that it may be repositioned relative to the deployment location. To the extent that a nested stabilizer encompassed by the present invention engages the proximal end of the stent, until that proximal end has been deployed, the stabilizer configuration may enable retraction of the stent relative to the sheath in a direction opposite the deployment location. So, for instance, when it is discovered prior to complete deployment that the stent is not in the desired location or not deploying correctly, the stent may be recaptured within the sheath by retracting the stabilizer or otherwise moving the sheath relative to, the stent to envelop the stent again, at which time the deployment process may be re-initiated. Thus, the term "stabilizer" should not be read to mean that it is only capable of resisting movement of the stent in one direction. The stabilizer of the present invention can also be used to transmit a longitudinal force to the low-column strength segment in the distal or proximal direction whenever the stent needs to be moved relative to an outer sheath, including when the stent is being loaded in the sheath.

In addition to the heat-resistant qualities of PEEK and PI making these polymers especially well-suited as materials of construction for sheath 40 in the embodiment shown in FIG. 7, the high tensile yield of PEEK and PI also make these polymers particularly well-suited for sheath materials for any of the embodiments described herein and shown generally in FIGS. 2A and 2B. In particular, sheath materials having a high tensile yield are preferred. Ideally, the sheath material has a tensile yield higher than the longitudinal force transmitted to the sheath by the stabilizer, such that the sheath does not stretch during deployment of the stent.

While the present invention has been described with respect to specific embodiments thereof, it is not limited thereto. Therefore, the claims that follow are intended to be construed to encompass not only the specific embodiments described but also all modifications and variants thereof which embody the essential teaching thereof.

What is claimed:

1. A stabilizer having a stent-underlying portion adapted to be disposed within an interior space defined by an inner periphery of a stent, the stent-underlying portion having a distal end adapted to be positioned adjacent a distal end of the stent, a proximal end adapted to be positioned adjacent a proximal end of the stent, and a length extending from the portion distal end to the portion proximal end, the stabilizer comprising a non-inflatable inner core and one or more members for engaging the stent inner periphery along the stent-underlying portion, wherein the one or more members for engaging the stent inner periphery comprises one or more radial protuberances that protrude from the inner core and lie along the stent-underlying portion of the stabilizer, wherein the one or more radial protuberances comprise at least two sets of rings about the inner core, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern.

2. The stabilizer of claim 1, wherein the one or more radial protuberances are axially distributed along the stent-underlying portion of the stabilizer along the length of the stent.

3. The stabilizer of claim 1, wherein the plurality of radial protuberances are positioned peripherally about the stabilizer such that the stabilizer engages the inner periphery of the stent in a plurality of peripheral locations.

4. The stabilizer of claim 1, wherein the radial protuberances are adapted to frictionally engage the stent inner periphery.

5. A stabilizer having a stent-underlying portion adapted to be disposed within an interior space defined by an inner periphery of a stent, the stent-underlying portion having a distal end adapted to be positioned adjacent a distal end of the stent, a proximal end adapted to be positioned adjacent a proximal end of the stent, and a length extending from the portion distal end to the portion proximal end, the stabilizer comprising a non-inflatable inner core and at least two sets of rings extending radially outwardly from the inner core for engaging the stent inner periphery along the length of the stent-underlying portion, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern, and wherein the rings for engaging the stent inner periphery comprises an outer surface of the stabilizer adapted to frictionally engage the stent inner periphery without protruding though interstitial openings in the stent inner periphery when the stent is disposed over the stabilizer in a predeployed condition.

6. The stabilizer of claim 5, wherein the stabilizer outer surface comprises a higher coefficient of static friction than both a coefficient of static friction and a coefficient of dynamic friction of the sheath.

7. The stabilizer of claim 5, wherein the stabilizer outer surface comprises a continuous member that extends from the distal end to the proximal end of the stent in contact with the inner periphery of the stent.

8. The stabilizer of claim 5, wherein the stabilizer comprises an inner core and the outer surface comprises a covering over the inner core.

9. The stabilizer of claim 8, wherein the covering comprises a coating on the inner core.

10. The stabilizer of claim 8, wherein the covering comprises a sleeve affixed to the inner core.

11. The stabilizer of claim 8, wherein the stabilizer comprises a plurality of discrete rings of the covering affixed to the inner core and a plurality of uncovered portions of the inner core spaced between the rings.

12. A stent delivery system comprising:
  a) a stent comprising a proximal end, a distal end, a length between the proximal end and the distal end, and an inner periphery that defines an interior space, the stent adapted to be a radially compressed and loaded within the delivery system for introduction into the body lumen and to be expanded for deployment within the body lumen;
  b) a sheath overlying the compressed stent during introduction of the stent within the body lumen;
  c) a stabilizer having a stent-underlying portion adapted to be disposed within the interior space of the stent, the stent-underlying portion having a distal end adapted to be positioned adjacent the distal end of the stent, a proximal end adapted to be positioned adjacent the proximal end of the stent, and a length extending from the portion distal end to the portion proximal end, the stabilizer comprising a non-inflatable inner core and one or more members, each of the one or more members comprising one or more radial protuberances that protrude from the inner core, wherein the one or more radial protuberances comprise at least two sets of rings about the inner core that engage the stent inner periphery, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern.

13. The stent delivery system of claim 12, wherein the stabilizer is adapted to hold the stent in a desired position when the sheath is moved relative to the stent.

14. The stent delivery system of claim 12 wherein the stabilizer is adapted to hold the stent in the desired position when the sheath is retracted to deploy the stent.

15. The stent delivery system of claim 12, wherein the stabilizer is adapted to hold the stent in the desired position when the sheath is advanced to recapture a partially-deployed stent.

16. The stent delivery system of claim 12, wherein the one or more radial protuberances are axially distributed along the stent-underlying portion from the distal end to the proximal end of the stent.

17. The stent delivery system of claim 16, wherein the stent comprises a framework having one or more areas of open space and at least one of the plurality of radial protuberances penetrates the open space.

18. A stabilizer having a stent-underlying portion adapted to be disposed within an interior space defined by an inner periphery of a stent, the stent-underlying portion having a distal end adapted to be positioned adjacent a distal end of the stent, a proximal end adapted to be positioned adjacent a proximal end of the stent, and a length extending from the portion distal end to the portion proximal end, the stabilizer comprising a non-inflatable inner core and one or more members for engaging the stent inner periphery, wherein the one or more members for engaging the stent inner periphery comprises at least two sets of rings extending radially outwardly from an outer surface of the stabilizer adapted to frictionally engage the stent inner periphery along the stent-underlying portion without protruding though interstitial openings in the stent inner periphery, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern.

19. A stabilizer for deployment of a stent in a distal location inside a body lumen from a proximal access location outside the body, the stabilizer having a stent-underlying portion adapted to be disposed within an interior space defined by an inner periphery of the stent, the stent-underlying portion having a distal end adapted to be positioned adjacent a distal end of the stent, a proximal end adapted to be positioned adjacent a proximal end of the stent, and a length extending from the portion proximal end to the portion distal end, the stabilizer comprising a non-inflatable inner core having a first diameter adapted to underlie the stent, a proximal shoulder not underlying the stent located adjacent the proximal end of the stent and having a second diameter, and at least one distal protuberance underlying the stent and protruding from the inner core for engaging the stent inner periphery without protruding through interstitial openings in the stent inner periphery when the stent is disposed over the stabilizer in a predeployed condition, wherein the at least one distal protuberance comprises at least two sets of rings about the inner core, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern.

20. The stabilizer of claim 19 further comprising a plurality of intermediate protuberances distributed between the proximal shoulder and the distal protuberance.

21. A stent delivery system for deployment of a stent in a distal location inside a body lumen from a proximal access location outside the body, the system comprising:
   a) a stent comprising a proximal end, a distal end, and an inner periphery that defines an interior space, the stent adapted to be radially compressed and loaded within the delivery system for introduction into the body lumen and to be expanded for deployment within the body lumen;
   b) a sheath overlying the compressed stent during introduction of the stent within the body lumen;
   c) a stabilizer having a stent-underlying portion adapted to be disposed within the interior space of the stent, the stent-underlying portion having a distal end adapted to be positioned adjacent the distal end of the stent, a proximal end adapted to be positioned adjacent a proximal end of the stent, and a length extending from the portion proximal end to the portion distal end, the stabilizer further comprising a non-inflatable inner core having a first diameter underlying the stent, a proximal shoulder not underlying the stent located adjacent the proximal end of the stent and extending to a proximal end of the stabilizer, and having a second diameter greater than the first diameter, and at least one member underlying the stent and protruding from the inner core and engaging the stent inner periphery without protruding through interstitial openings in the stent inner periphery, wherein the at least one member comprises at least two sets of rings about the inner core, wherein each set of rings includes at least two rings, each of the at least two rings adjacently positioned, the rings in a first set positioned along a length of the stent-underlying portion extending from the portion's distal end to the portion's proximal end and spaced in a first pattern, and the rings in a second set positioned at either the distal end of the stent-underlying portion or the proximal end of the stent-underlying portion and spaced in a second pattern that is different than the first pattern.

22. The stent delivery system of claim 21, wherein the stabilizer further comprises a plurality of intermediate protuberances distributed between the proximal shoulder and the distal protuberance.

* * * * *